United States Patent
Riermeier et al.

(10) Patent No.: US 6,437,175 B2
(45) Date of Patent: Aug. 20, 2002

(54) PROCESS FOR RACEMIZATION OF N-ACYLAMINO ACIDS BY MEANS OF TRANSITION METAL CATALYSTS

(75) Inventors: Thomas Riermeier, Flörsheim; Matthias Beller, Rostock; Daniel Schichl, Garching, all of (DE); Martin Hateley, Nr. Stourbridge (GB)

(73) Assignee: Aventis Research & Technologies GmbH & Co KG (DE)

( * ) Notice: Subject to any disclaimer, the term of this patent is extended or adjusted under 35 U.S.C. 154(b) by 0 days.

(21) Appl. No.: 09/803,688

(22) Filed: Mar. 12, 2001

(30) Foreign Application Priority Data

Mar. 18, 2000 (DE) .......................................... 100 13 599

(51) Int. Cl.$^7$ ............................................. C07B 55/00
(52) U.S. Cl. ...................................................... 562/401
(58) Field of Search ......................... 564/302; 562/553, 562/554

(56) References Cited

U.S. PATENT DOCUMENTS

| | | | |
|---|---|---|---|
| 3,692,775 A | * | 9/1972 | Kubanek et al. |
| 4,182,904 A | | 1/1980 | Franzmann et al. ........ 562/401 |
| 4,638,086 A | | 1/1987 | Grabley ..................... 562/401 |

FOREIGN PATENT DOCUMENTS

| | | |
|---|---|---|
| DE | 2740380 | 3/1979 |
| DE | 3334849 | 4/1985 |

OTHER PUBLICATIONS

Beller, et al, Palladium–Catalyzed Amidocarbonylation–A New, Efficient Synthesis of N–Acyl Amino Acids, 1997, Angewandte Chemie International Edition, 36 (13/14), pp. 1494–1496.*

Greenstein, J. P., et al, *Chemistry of the Amino Acids*, London, John Wiley & Sons, 1961, vol. 1, pp. 715–760.

Chikara Hongo, et al, "Asymmetric Transformation of N–Acyl–DL–amino Acids," *Bull. Chem. Soc. Jpn* 54: 3286–3290 (1981).

Schollkopf, U., "Enantioselective Synthesis of Nonproteinogenic Amino Acids," *Top. Curr. Chem. 109*:65–84 (1983).

Evans, D. A., et al, "Synthesis of the CyclicHexapeptide Echinocandin D. New Approaches to the Asymmetric Synthesis of β–Hydroxy α–Amino Acids," *J. Am. Chem. Soc. 109*:7151–7157 (1987).

Williams, R. M., et al, Practical Asymmetric Synthesis of –Amino Acids through Carbon–Carbon Bond Constructions on Electrophilic Glycine Templates, *J.Am.Chem.Soc. 110*;1547–57 (1988).

Chenault, H.K.,et al, "Kinetic Resolution of Unnatural and Rarely Occurring Amino Acids: Enantioselective Hydrolysis of N–Acyl Amino Acids Catalyzed by Acylase I" *J. Am. Chem. Soc. 111*:6354–6364 (1989).

Evans, D. A., "The Asymmetric Synthesis of α–Amino Acids, Electrophilic Azidation of Chiral Imide Enolates, a Practical Approach to the Synthesis of (R)–and (S)–α–Azido Carboxylic Acids" *J. Am. Chem. Soc. 112*:4011–4030 (1990).

Trost, B. M., "The Atom Exonomy–A Search for Synthetic Efficiency" *Science 254*:1471–1477 (1991).

Seebach, D., et al, "Die Selbstregeneration von stereozentren (SRS)—Anwendungen, Grenzen und Preisgabe eines Syntheseprinzips," *Angew. Chem. 108*:2881–2921 (1996).

Myers, A. G. et al, "Highly Practical Methodology for the Synthesis of D–and L–α–Amino Acids, N–Protected α–Amino Acids, and N–Methyl–α–amino Acids," *J. Am. Chem. Soc. 119*:656–673 (1997).

Petasis, N. A., et al, "A New and Practical Snythesis of α–Amino Acids from alkenyl Boronic Acids," *J. Am. Chem. Soc. 119*:445–446 (1997).

Park, Y. S., et al, "Enantioselective Synthesis of α–,β–, and γ–Aryl Amino Acids and Esters," *J. Org. Chem. 62*:1574–75 (1997).

* cited by examiner

*Primary Examiner*—Johann Richter
*Assistant Examiner*—Paul A. Zucker
(74) *Attorney, Agent, or Firm*—Connolly Bove Lodge & Hutz LLP

(57) ABSTRACT

The present invention relates to a process for the racemization of N-acylamino acids of the formula (I)

R—CH(NR$^1$COR$^2$)CO$_2$H     (I)

in which, in a solvent, an enantiomerically enriched mixture or an enantiomerically pure compound of the formula (I) is reacted in the presence of a transition metal salt, transition metal complex or transition metal complex salt or of a mixture thereof comprising at least one element from the group consisting of Fe, Ru, Os, Co, Rh, Ir, Ni, Pd, Pt, preferably at a temperature of 10-150° C.

19 Claims, No Drawings

PROCESS FOR RACEMIZATION OF N-ACYLAMINO ACIDS BY MEANS OF TRANSITION METAL CATALYSTS

This application claims benefit to German application number 100 13 599.4 filed Mar. 17, 2000.

DESCRIPTION

The invention relates to a process for the racemization of enantiomerically pure N-acylamino acids using transition metal catalysts for the preparation of racemic N-acylamino acids of the formula (I).

Amino acids and their derivatives indisputably belong to the most important classes of organic compound. In addition to the biochemical importance, amino acid derivatives are of great economic interest as active compound intermediates, agrochemicals, food additives and industrial fine chemicals. Despite the development of enantioselective preparation processes, for example, by Schöllkopf (U. Schöllkopf, *Top. Curr. Chem.* 1983, 109, 65), Seebach (D. Seebach, A. R. Sting, M. Hoffmann, *Angew. Chem.* 1996, 108, 2880), Evans (D. A. Evans, A. E. Weber, *J. Am. Chem. Soc.* 1987, 109, 7151; D. A. Evans, T. C. Britton, J. A. Ellman, R. L. Dorow, *J. Am. Chem. Soc.* 1990, 112, 4011), Williams (R. M. Williams, P. J. Sinclair, D. Zhai, D. Chen, *J. Am. Chem. Soc.* 1988, 110, 1547; R. M. Williams, Vol. 7, Pergamon Press 1989) and the newest method developments (N. A. Petasis, I. A. Zavialov, *J. Am. Chem. Soc.* 1997, 119, 445–446; Y. S. Park, P. Beak, *J. Org. Chem.* 1997, 62, 1574–1575; A. G. Myers, J. L. Gleason, T. Yoon, D. W. Kung, *J. Am. Chem. Soc.* 1997, 119, 656–673; B. M. Trost, *Science* 1991, 254, 1471–1477), in general "classical methods" such as the Strecker synthesis with subsequent N-acylation and resolution are used industrially for the preparation of unnatural amino acids. The advantage of three-stage processes of this type is in particular in the price and the availability of the starting materials and the practicability of the individual reaction steps.

Enzymatic resolutions of various N-acylamino acids are possible with a large number of functionalized N-acylamino acids in the presence of acylases. Compilations are found, for example, in J. P. Greenstein, M. Winitz in "Chemistry of the Amino Acids" John Wiley & Sons, London, 1961, Vol 1, 715–760; H. Keith, J. Dahmer, G. M. Whitesides, *J. Am. Chem. Soc*, 1989, 111, 6354–6364. Generally, in the resolution processes the undesired remaining enantiomer of the N-acylamino acid is racemized again after the resolution, so that in a multistage process almost quantitative yields of the desired enantiomerically pure amino acid are achieved. In the literature, to date acid catalysts are employed at relatively high temperatures as racemization catalysts for N-acylamino acids (DE 3334849). On account of the drastic reaction conditions and the nonspecific reactivity of the acid catalysts, in the case of sensitive functionalized N-acylamino acids side reactions occur which decrease the total yield and significantly complicate the product isolation. Alternatively to this, racemization can be carried out using stoichiometric amounts of ketene (DE 2740380). Because of the high toxicity and the impracticable manipulability of ketene, this method, however, is scarcely of practical use.

Against this background, the development of novel gentle racemization catalysts is of great interest. The object of the present invention was consequently to make available a process for the racemization of N-acylamino acids which proceeds under mild conditions.

Surprisingly, it has been found that enantiomerically pure or enantiomerically enriched N-acylamino acids can be racemized at the stereogenic center ($\alpha$-C center) under mild reaction conditions in the presence of transition metal catalysts.

The subject of the present invention is a process for the racemization of N-acylamino acids of the formula (I),

$$R\text{—}CH(NR^1COR^2)CO_2H \qquad (I)$$

in which R, $R^1$ and $R^2$ independently of one another are a hydrogen and/or alkyl, alkenyl, alkynyl, aryl and/or heteroaryl radical, where alkyl can be an aliphatic carbon group having 1 to 18 carbon atoms, which can be linear, branched and/or alternatively cyclic, and alkenyl or alkynyl is a mono- or polyunsaturated aliphatic group having 2 to 18 carbon atoms, which can be branched or nonbranched, and aryl is a five-, six- or seven-membered aromatic ring, where this ring can be fused and can contain 0 to 3 heteroatoms such as N, O, S, comprising 4 to 14 carbon atoms, and in this case the alkyl and the aryl group can optionally carry up to six further substituents which independently of one another are hydrogen, alkyl, O-alkyl, OCO-alkyl, O-aryl, aryl, fluorine, chlorine, bromine, iodine, OH, $CF_3$, $NO_2$, NO, Sialkyl$_3$, CN, COOH, CHO, $SO_3H$, $NH_2$, NH-alkyl, N-alkyl$_2$, PO-alkyl$_2$, $SO_2$-alkyl, SO-alkyl, $CF_3$, NHCO-alkyl, $CONH_2$, CO-alkyl, COO-alkyl, NHCOH, NHCOO-alkyl, CO-aryl, COO-aryl, POaryl$_2$, $PO_3H_2$, PO(O-alkyl)$_2$, $SO_3$-alkyl, where alkyl and aryl have the abovementioned meaning, which comprises reacting, in a solvent, an enantiomerically enriched mixture or an enantiomerically pure compound of the formula (I), in the presence of a transition metal salt, transition metal complex or transition metal complex salt or of a mixture thereof comprising at least one element from the group consisting of Fe, Ru, Os, Co, Rh, Ir, Ni, Pd, Pt, preferably at a temperature of 10–150° C.

By a combination of the catalytic racemization described here with a crystallization of an enantiomer in the presence of a chiral resolution reagent or with an acylase-catalyzed deacylation, for the first time dynamic kinetic resolutions of racemic N-acylamino acids can also be carried out.

The process according to the invention can moreover be carried out very economically and both simply and rapidly. After completion of the reaction, the racemized product is purified by simple measures, e.g. by extraction or crystallization, or it is subjected directly as a crude product to a resolution, such as, for example, reaction with an acylase, crystallization using a chiral resolution reagent, such as a chiral base or direct crystallization. If appropriate, such a process can also be carried out in situ, so that a dynamic kinetic resolution results.

Further, with the aid of the method found an asymmetric transformation of N-acylamino acids, such as is described, for example, in *Bull. Chem. Soc. Jpn.* 1981, 54, 3286, can be carried out under markedly milder and more gentle conditions.

Preferably, in the compounds of the formula (I) R, $R^1$ and $R^2$ independently of one another are hydrogen, ($C_4$-$C_{14}$)-aryl, ($C_1$-$C_{18}$)-alkyl, ($C_2$-$C_{18}$)-alkenyl or ($C_3$-$C_{18}$)-alkynyl, $C_nH_{2n}$-cycloalkyl where n=3–18, which can be branched or nonbranched and which can be substituted by 1–6 substituents which independently of one another are hydrogen, alkyl, O-alkyl, O-aryl, aryl, fluorine, chlorine, bromine, iodine, OH, $NO_2$, CN, COOH, CHO, $NH_2$, NH-alkyl, N-alkyl$_2$, PO-alkyl$_2$, $SO_2$-alkyl, $CF_3$, NHCO-alkyl, $CONH_2$, CO-alkyl, NHCOH, NHCOO-alkyl, CO-aryl, COO-aryl, POaryl$_2$, PO$_3$H$_2$, PO(O-alkyl)$_2$, and aryl is a five-, six- or seven-membered aromatic ring, where this ring can be fused and can contain 0 to 3 heteroatoms such as N, O, S, comprising 4 to 14 carbon atoms.

Particularly preferably, in the compounds of the formula (I)

R, R$^1$ and R$^2$ independently of one another are hydrogen, (C$_5$-C$_{12}$)-aryl, (C$_1$-C$_{16}$)-alkyl, (C$_2$-C$_{16}$)-alkenyl or (C$_3$-C$_{16}$)-alkynyl, C$_n$H$_{2n}$-cycloalkyl where n=3–16, which can be branched or nonbranched and which can be substituted by 1–4 substituents which independently of one another are hydrogen, alkyl, O-alkyl, O-aryl, aryl, fluorine, chlorine, bromine, iodine, OH, NO$_2$, CN, COOH, CHO, NH$_2$, NH-alkyl, N-alkyl$_2$, CF$_3$, NHCO-alkyl, CONH$_2$, CO-alkyl, NHCOH, NHCOO-alkyl, CO-aryl, COO-aryl, and aryl is a five-, six or seven-membered aromatic ring, where this ring, can be fused and can contain 0 to 3 heteroatoms such as N, O, S, comprising 4 to 12 carbon atoms.

Very particularly preferably, in the compounds of the formula (I)

R, R$^1$ and R$^2$ independently of one another are hydrogen, (C$_5$-C$_{10}$)-aryl, (C$_1$ C$_{14}$)-alkyl, (C$_2$-C$_{14}$)-alkenyl or (C$_3$-C$_{14}$)-alkynyl, C$_n$H$_{2n}$-cycloalkyl where n=3–14, which can be branched or nonbranched and which can be substituted by 1–3 substituents which independently of one another are hydrogen, alkyl, O-alkyl, O-aryl, aryl, fluorine, chlorine, bromine, iodine, OH, NO$_2$, CN, COOH, CHO, NH$_2$, NH-alkyl, N-alkyl$_2$, CF$_3$, NHCO-alkyl, CONH$_2$, CO-alkyl, CO-aryl, COO-aryl, and aryl is a five-, six- or seven-membered aromatic ring, where this ring can be fused and can contain 0 to 3 heteroatoms such as N, O, S, comprising 4 to 10 carbon atoms.

Examples of N-acylamino acids which can be racemized by the process according to the invention, without these being restricted thereto, are: N-acylvaline, N-acylvinylglycine, N-acylphenylalanine, N-acylmethionine, N-acylphenylglycine, N-acyl-4-hydroxyphenylglycine, N-acyl-3-pyridylalanine, N-acyltryptophan, N-acyllysine, N-acyl-tert-leucine, N-acylproline, N-acylcyclohexylglycine, N-acylserine, N-acylphosphinothricin. In this case, acyl is preferably acetyl, benzoyl, phenylacetyl, methoxyacetyl, chloroacetyl, and propionyl.

Preferably, the racemization catalysts used are salts, complexes or salts of the complexes of the transition metals Fe, Ru, Ir, Rh, Co and Pd.

Particularly preferred racemization catalysts are compounds of the elements Ru, Ir, Rh, Pd. Examples of complexes of these elements which can be employed are: [Rh(cod)Cl]$_2$, (CO)$_2$Rhacac, Rh(cod)acac, Rh(PPh$_3$)$_3$Cl, Ir(PPh$_3$)$_3$Cl, [Ru(p-cymene)Cl]$_2$, Rh(cod)$_2$BF$_4$, [Ru(CO)$_2$CH$_3$CO$_2$]$_n$, Ru(CO)(H$_2$)(PPh$_3$)$_3$, Ru(cod)Cl$_2$, Ir(cod)$_2$BF$_4$, IrCl(CO)(PPh$_3$)$_2$, Ir(CO)$_2$acac, Ru(acac)$_3$, Pd(PPh$_3$)$_4$, PdCl$_2$(CH$_3$CN)$_2$, Pd(OAc)$_2$, PdCl$_2$, Li$_2$PdCl$_4$, Pd$_2$(dba)$_3$.

As a rule, it is advantageous if the racemization catalyst is present in homogeneous form. However, heterogeneous or heterogenized metal complexes can advantageously be employed, in particular at reaction temperatures of >100° C. Heterogeneous catalysts to be employed are, for example, rhodium, iridium or ruthenium on supports such as activated carbon, alumina, silica gel and titanium dioxide. For the stabilization but also for increasing the activity of the catalysts, the addition of nitrogen-containing and/or phosphorus-containing ligands, such as of amine and/or phosphine ligands, is advantageous. Typically employed phosphine ligands are triphenylphosphine, tricyclohexylphosphine, tri(tert-butyl)phosphine, TPPTS (tris(3-sulfonatophenyl)phosphine), tri-n-butylphosphine, bisdiphenylphosphinopropine, tri-o-tolylphosphine, trimethyl phosphate, diphenyl-2-pydridyl-phosphine, and bis (dicyclohexylphosphino)butane. Amine ligands which can be used, for example, are triethylamine, pyridine, bipyridine, tetramethylethylenediamine, triazacyclononane, and piperazine.

The reaction is expediently carried out in a solvent. Solvents which can be used are organic solvents or water. It may be advantageous to use mixtures of solvents. Suitable solvents are, for example, acetonitrile, butyronitrile, ethyl acetate, dimethoxyethane, acetone, THF, dioxane, hexane, tert-butyl methyl ether and tert-butanol, toluene, DMSO, chloroform and respective mixtures thereof. The proportion of N-acylamino acid in the solution is preferably 5–50%.

The N-acylamino acids are expediently prepared from the amino acid by known methods of acylation.

In the process according to the invention, the racemization catalyst is preferably employed in catalytic amounts with respect to the N-acylamino acid. Generally, between 0.2 and 0.0001 equivalent based on N-acylamino acid, preferably 0.15 to 0.001 and particularly preferably 0.1 to 0.001 equivalent, is used.

The present invention is to be illustrated in greater detail by means of the following examples, without restricting the invention thereto.

EXAMPLES

1) Racemization of (S)-N-acetylvaline
2) Racemization of (S)-N-acetylproline
3–5) Racemization of (S)-N-acetylphenylalanine
6–12) Racemization of (S)-N-acetylphenylalanine using various catalyst systems All isolated products or crude product mixtures were identified by $^1$H-NMR and mass spectra or by HPLC.

The optical purity of the products was determined by HPLC, e.g. on Chiralpak AD 250×4.6 (Daicel).

Example 1:

A solution of (S)-N-acetylvaline (83.7 mg, 0.483 mmol), tricyclohexylphosphane (67.7 mg, 0.242 mmol), [Rh(cod)Cl]$_2$ (11.9 mg, 0.0242 mmol) in 10 ml of acetonitrile is heated at 60° C. for 48 hours. The solvent is then removed, 10 ml of an aqueous 1 N NaOH solution is added and the mixture is extracted with ethyl acetate (3×10 ml). The aqueous phase is acidified with sulfuric acid and N-acetylvaline is extracted with ethyl acetate (3×20 ml). The organic phase is dried over MgSO$_4$. After removing the solvent in vacuo, N-acetylvaline having an enantiomeric excess of 8.0% (by means of GC, ee value of the methyl ester derivative) is obtained.

Example 2:

A solution of (S)-N-acetylproline (75.9 mg, 0.483 mmol), tricyclohexylphosphane (67.7 mg, 0.242 mmol) and [Rh(cod)Cl]$_2$ (11.9 mg, 0.0242 mmol) in 10 ml of acetonitrile is heated at 60° C. for 48 hours. After working up (see Example 1), N-acetylproline having an enantiomeric excess of 1.0% (by means of GC, ee value of the methyl ester derivative) is obtained.

Example 3:

A solution of (R)-N-acetylphenylalanine (100 mg, 0.483 mmol), triphenylphosphane (63.2 mg, 0.242 mmol) and [Rh(cod)Cl]$_2$ (11.9 mg, 0.0242 mmol) in 10 ml of acetonitrile is heated at 60° C. for 48 hours. After working up (see Example 1), N-acetylphenylalanine having an enantiomeric excess of 34.0% (by means of GC, ee value of the methyl ester derivative) is obtained.

Example 4:

A solution of (S)-N-acetylphenylalanine (100 mg, 0.483 mmol), tricyclohexylphosphane (67.7 mg, 0.242 mmol) and [Rh(cod)Cl]$_2$ (11.9 mg, 0.0242 mmol) in 10 ml of toluene is heated at 100° C. for 48 hours. After working up (see Example 1), N-acetylphenylalanine having an enantiomeric excess of 5.4% (by means of GC, ee value of the methyl ester derivative) is obtained.

Example 5:

A solution of (S)-N-acetylphenylalanine (100 mg, 0.483 mmol), tricyclohexylphosphane (67.7 mg, 0.242 mmol), [Rh(cod)Cl]$_2$ (11.9 mg, 0.0242 mmol) and tetrabutylammonium bromide (15.6 mg, 0.048 mmol) in 10 ml of acetone is heated at 50° C. for 48 hours. After working up (see Example 1), N-acetylphenylalanine having an enantiomeric excess of 17.0% (by means of GC, ee value of the methyl ester derivative) is obtained.

Examples 6–12:

A solution of (S)-N-acetylphenylalanine (100 mg, 0.483 mmol), tricyclohexylphosphane (67.7 mg, 0.242 mmoland 5 mol % of catalyst in 10 ml of acetonitrile is heated at 60° C. for 48 hours. For results see Table 1.

TABLE 1

Racemization of (S)-N-acetylphenylalanine using various catalysts.

| Example | Catalyst | Solvent | Temp [° C.] | Reaction time [h] | ee value |
|---|---|---|---|---|---|
| 6 | [Rh(cod)Cl]$_2$ | MeCN | 60 | 48 | 0.4–10.3% |
| 7 | [Rh(nbd)Cl]$_2$ | MeCN | 60 | 48 | 18% |
| 8 | [Rh(cod)$_2$BF$_4$] | MeCN | 60 | 48 | 50% |
| 9 | (CO)$_2$Rh(acac) | MeCN | 60 | 48 | 74% |
| 10 | RhCl$_3$xH$_2$O | MeCN | 60 | 48 | 70% |
| 11[a] | [Rh(cod)Cl]$_2$ | MeCN | 60 | 20 | 26% |
| 12 | [Rh(cod)Cl]$_2$ | MeCN | 60 | 20 | 30% |

[a](R)-N-acetylphenylalanine was used.

Preliminary Remarks on Examples 13–20

The following reactions were carried out:

13–17) Racemization of (S)-N-acetylphenylalanine using various palladium catalysts 18) Racemization of (S)-N-acetylleucine using Pd(OAc)$_2$/PPh$_3$ 19) Racemization of (S)-N-acetylmethionine using Pd(OAc)$_2$/PPh$_3$ 20) Racemization of (S)-N-acetylproline using Pd(OAc)$_2$/PPh$_3$ All isolated products or crude product mixtures were identified by 1H-NMR and mass spectra or by HPLC.

The optical purity of the products was determined by HPLC, e.g. on Chiralpak AD 250×4.6 (Daicel).

Example 13:

A solution of (S)-N-acetylphenylalanine (100 mg, 0.483 mmol) and Pd(PPh$_3$)$_4$ (5.6 mg, 0.00483 mmol) in 10 ml of acetonitrile is heated at 60° C. for 48 hours. After working up (see Example 1), N-acetylphenylalanine having an enantiomeric excess of 14.0% (by means of GC, ee value of the methyl ester derivative) is obtained.

Example 14:

A solution of (S)-N-acetylphenylalanine (100 mg, 0.483 mmol), triphenylphosphane (6.3 mg, 0.02415 mmol) and Pd(OAc)$_2$ (1.08 mg, 0.00483 mmol) in 10 ml of acetonitrile is heated at 60° C. for 48 hours. After working up (see Example 1), N-acetylphenylalanine having an enantiomeric excess of 8.0% (by means of GC, ee value of the methyl ester derivative) is obtained.

Example 15:

A solution of (S)-N-acetylphenylalanine (100 mg, 0.483 mmol), triphenylphosphane (6.3 mg, 0.02415 mmol) and Pd(OAc)$_2$ (1.08 mg, 0.00483 mmol) in 10 ml of acetonitrile is heated at 80° C. for 48 hours. After working up (see Example 1), N-acetylphenylalanine having an enantiomeric excess of 3.0% (by means of GC, ee value of the methyl ester derivative) is obtained.

Example 16:

A solution of (S)-N-acetylphenylalanine (100 mg, 0.483 mmol), tricyclohexylphosphane (6.8 mg, 0.02415 mmol) and Pd(OAc)$_2$ (1.08 mg, 0.00483 mmol) in 10 ml of acetonitrile is heated at 60° C. for 48 hours. After working up (see Example 1), N-acetylphenylalanine having an enantiomeric excess of 76.0% (by means of GC, ee value of the methyl ester derivative) is obtained.

Example 17:

A solution of (S)-N-acetylphenylalanine (100 mg, 0.483 mmol), triphenylphosphane (6.3 mg, 0.02415 mmol) and Pd$_2$(dba)$_3$ (2.21 mg, 0.00483 mmol) in 10 ml of acetonitrile is heated at 80° C. for 48 hours. After working up (see Example 1), N-acetylphenylalanine having an enantiomeric excess of 1.0% (by means of GC, ee value of the methyl ester derivative) is obtained.

Example 18:

A solution of (S)-N-acetylleucine (83.7 mg, 0.483 mmol), triphenylphosphane (6.3 mg, 0.02415 mmol) and Pd(OAc)$_2$ (1.08 mg, 0.00483 mmol) in 10 ml of acetonitrile is heated at 80° C. for 48 hours. After working up (see Example 1), (S)-N-acetylleucine having an enantiomeric excess of 13.0% (by means of GC, ee value of the methyl ester derivative) is obtained.

Example 19:

A solution of (S)-N-acetylmethionine (92.4 mg, 0.483 mmol), triphenylphosphane (15.8 mg, 0.0604 mmol) and Pd(OAc)$_2$ (2.7 mg, 0.0121 mmol) in 10 ml of acetonitrile is heated at 60° C. for 48 hours. After working up (see Example 1), (S)-N-acetylmethionine having an enantiomeric excess of 9.0% (by means of GC, ee value of the methyl ester derivative) is obtained.

Example 20:

A solution of (S)-N-acetylproline (75.9 mg, 0.483 mmol), triphenylphosphane (6.3 mg, 0.02415 mmol) and Pd(OAc)$_2$ (1.08 mg, 0.00483 mmol) in 10 ml of acetonitrile is heated at 80° C. for 48 hours. After working up (see Example 1), (S)-N-acetylproline having an enantiomeric excess of 10.0% (by means of GC, ee value of the methyl ester derivative) is obtained.

What is claimed is:

1. A process for the catalytic racemization of N-acylamino acid of the formula (I)

R—CH(NR$^1$COR$^2$)CO$_2$H     (I)

in which R, R$^1$ and R$^2$ independently of one another are a hydrogen, optionally substituted alkyl, alkenyl, alkynyl, optionally substituted aryl of optionally substituted heteroaryl radical, which comprises reacting, in a solvent, an enantiomerically enriched mixture or an enantiomerically pure compound of the formula (I), a phosphorus-containing ligand in the presence of a racemization catalyst comprising a transition metal salt, a transition metal complex or a transition metal complex salt or of a mixture thereof wherein said transitional metal salt and said transitional metal complex comprises at least one element selected from the group consisting of Fe, Ru, Os, Co, Rh, Ir, Ni, Pd, and Pt and said reaction occurs at a reaction temperature at 100° C. or less.

2. The process as claimed in claim 1, wherein said aryl or said heteroaryl has a ring which is optionally fused and said heteroaryl contains up to 3 heteroatoms and said alky and said aryl group can optionally carry up to six further substituents which independently of one another are hydrogen, alkyl, O-alkyl, OCO-alky, O-aryl, aryl, fluorine, chlorine, bromine, iodine, OH, $CF_3$, $NO_2$, NO, $Sialkyl_3$, CN, COOH, CHO, $SO_3H$, $NH_2$, NH-alkyl, N-$alkyl_2$, PO-$alkyl_2$, $SO_2$-alkyl, SO-alkyl, $CF_3$, NHCO-alkyl, $CONH_2$, CO-alkyl, COO-alkyl, NHCOH, NHCOO-alkyl, CO-aryl, COO-aryl, PO$aryl_2$, $PO_3H_2$, PO(O-alkyl)$_2$ or $SO_3$-alkyl wherein said alkyl is 1 to 18 carbon atoms and said aryl is a 5 and 7 membered aromatic ring.

3. The process as claimed in claim 1, wherein said transition metal salt or said transition metal complex salt has transition metals, Fe, Ru, Ir, Rh, Co or Pd or mixtures thereof.

4. The process as claimed in claim 1, which further comprises adding a nitrogen-containing ligand to the reaction.

5. The process as claimed in claim 4, wherein said nitrogen-containing ligand is an amine ligand and said phosphorus-containing ligand is a phosphine ligand.

6. The process as claimed in claim 4, wherein said phosphorus-containing ligand is selected from the group consisting of triphenylphospine, tricyclohexylphosphine, tri(tert-butyl)phosphine, TPPTS (tris(3-sulfonatophenyl) phosphine), tri-n-butylphosphine, bisdiphenylphosphinopropane, tri-o-tolylphosphine, trimethyl phosphate, diphenyl-2-pydridylphosphine and bis(dicyclohexylphosphino)butane, and said nitrogen-containing ligand is selected from the group consisting of triethylamine, pyridine, bipyridine, tetramethylethylendiamine, triazacyclononane and piperazine.

7. The process as claimed in claim 1, where the reaction is carried out in water, in an organic solvent or a mixture thereof.

8. The process as claimed in claim 1, wherein said N-acylamino acid is in the solution in an amount from 5–50%.

9. The process as claimed in claim 1, wherein the racemization catalyst is employed in catalytic amounts of between 0.2 and 0.0001 equivalent based on the N-acylamino acid.

10. The process as claimed in claim 1, wherein the racemization catalyst is employed in catalytic amounts of between 0.1 to 0.001 equivalent based on the N-acylamino acid.

11. The process as claimed in claim 1, wherein the reaction is carried out at a temperature of 10 to 80° C.

12. The process as claimed in claim 1, wherein the reaction is carried out at a temperature of between 40and 80° C.

13. The process as claimed in claim 2, wherein the heteroatom is N, O or S.

14. The process as claimed in claim 3, wherein an amine ligand or a phosphine ligand is added to the reaction and the racemization catalyst is employed in catalytic amounts of between 0.1 to 0.0001 equivalent based on the N-acylamino acid and the reaction is carried out at a temperature of between 40 to 80° C.

15. The process as claimed in claim 14, wherein said alkyl is an aliphatic carbon group having 1 to 18 carbon atoms, which can be linear, branched and/or alternatively cyclic, and said alkenyl and said alkynyl different and are a mono- or polyunsaturated aliphatic group having 2 to 18 carbon atoms, which is branched or nonbranched, and aryl is a five-, six- or seven-membered aromatic ring.

16. The process as claimed in claim 1, wherein R, $R^1$ and $R^2$ independently of one another are hydrogen, ($C_5$–$C_{12}$)-aryl, ($C_1$–$C_{16}$)-alkyl, ($C_2$–$C_{16}$)-alkenyl or ($C_3$–$C_{16}$)-alkynyl, $C_2H_{2n}$-cycloalkyl where n=3–16, which is branched or nonbranched and which is optionally substituted by 1–4 substituents and wherein said substituents independently of one another are hydrogen, alkyl, O-alkyl, O-aryl, aryl, fluorine, chlorine, bromine, iodine, OH, $NO_2$, CN, COOH, CHO, $NH_2$, NH-alkyl, N-$alkyl_2$, $CF_3$, NHCO-alkyl, $CONH_2$, CO-alkyl, NHCOH, NHCOO-alkyl, CO-aryl, or COO-aryl, and said aryl is a five-, six or seven-membered aromatic ring, where said ring, is optionally fused and contains 0 to 3 heteroatoms selected from the group consisting of N, O and S, and said ring contains 4 to 12 carbon atoms.

17. The process as claimed in claim 1, wherein R, $R^1$ and $R^2$ independently of one another are hydrogen, ($C_5$–$C_{10}$)-aryl, ($C_1$–$C_{14}$)-alkyl, ($C_2$–$C_{14}$)-alkenyl or ($C_3$–$C_{14}$)-alkynyl, $C_nH_{2n}$-cycloalkyl where n=3–14, which is branched or nonbranched and which is optionally substituted by 1–3 substituents and wherein said substituents independently of one another are hydrogen, alkyl, O-alkyl, O-aryl, aryl, fluorine, chlorine, bromine, iodine, OH, $NO_2$, CN, COOH, CHO, $NH_2$, NH-alkyl, N-$alkyl_2$, $CF_3$, NHCO-alkyl, $CONH_2$, CO-alkyl, CO-aryl, or COO-aryl, and said aryl is a five-, six- or seven-membered aromatic ring, and said ring is optionally fused and said ring contains 0 to 3 heteroatoms selected from the group consisting of N, ) and S, and said ring contains 4 to 10 carbon atoms.

18. The process as claimed in claim 1, wherein the N-acylamino acid is selected from the group consisting of N-acylvaline, N-acylvinylglycine, N-acylphenylalanine, N-acylmethionine, N-acylphenylglycine, N-acyl-4-hydroxyphenylglycine, N-acyl-3-pyridylalanine, N-acyltryptophan, N-acyllysine, N-acyl-tert-leucine, N-acylproline, N-acylcyclohexylglycine, N-acylserine and N-acylphosphinothricin.

19. The process as claimed in claim 1, wherein the racemization catalyst is {Rh(cod)Cl}$_2$, (CO)$_2$Rhacac, Rh(cod)acac, Rh(PPH$_3$)$_3$Cl, Ir(PPH$_3$)$_3$Cl, {Ru(p-cymene)Cl]}2, Rh(cod)$_2$BF$_4$, Ru(CO)(H$_2$)(PPh$_3$)$_3$, Ru(cod)Cl$_2$, Ir(cod)$_2$BF$_4$, IrCl(CO)(PPh$_3$)$_2$, Ir(CO)$_2$acac, Ru(acac)$_3$, Pd(PPh$_3$)$_4$, PdCl$_2$(CH$_3$CN)$_2$, Pd(OAc)$_2$, PdCl$_2$, Li$_2$PdCl$_4$, Pd$_2$(dba)$_3$.

* * * * *

UNITED STATES PATENT AND TRADEMARK OFFICE
CERTIFICATE OF CORRECTION

PATENT NO. : 6,437,175 B2
DATED : August 20, 2002
INVENTOR(S) : Riermeier et al.

It is certified that error appears in the above-identified patent and that said Letters Patent is hereby corrected as shown below:

Column 6,
Line 55, delete "of" and insert -- or --.

Column 8,
Line 38, delete ")" and insert -- O --.

Signed and Sealed this

Twenty-sixth Day of November, 2002

Attest:

JAMES E. ROGAN
Attesting Officer
Director of the United States Patent and Trademark Office